US006595362B2

(12) United States Patent  (10) Patent No.: US 6,595,362 B2
Penney et al.  (45) Date of Patent: Jul. 22, 2003

(54) CASES FOR MEDICATION DELIVERY DEVICES

(75) Inventors: Melinda Penney, Providence, RI (US); Sherin Lussier, Providence, RI (US); Dalita R. Tomellini, Rehoboth, MA (US)

(73) Assignee: Lindon Products Inc., Providence, RI (US)

( * ) Notice: Subject to any disclaimer, the term of this patent is extended or adjusted under 35 U.S.C. 154(b) by 0 days.

(21) Appl. No.: 09/853,501

(22) Filed: May 11, 2001

(65) Prior Publication Data

US 2002/0050462 A1 May 2, 2002

Related U.S. Application Data

(60) Provisional application No. 60/203,880, filed on May 12, 2000.

(51) Int. Cl.[7] ................................................. B65D 85/20
(52) U.S. Cl. ........................ 206/364; 206/366; 206/523
(58) Field of Search ................................. 206/232, 364, 206/363, 365, 366, 370, 438, 443, 446, 470, 471, 523

(56) References Cited

U.S. PATENT DOCUMENTS

| 1,239,308 A | | 9/1917 | Scott |
|---|---|---|---|
| 1,644,830 A | * | 10/1927 | Henderson .................. 206/232 |
| 1,980,141 A | | 11/1934 | MacGregor |
| 2,108,492 A | * | 2/1938 | Lagier ......................... 206/229 |
| 2,753,094 A | * | 7/1956 | Haney, Jr. ................... 224/197 |
| 4,573,973 A | | 3/1986 | Mezi .......................... 604/197 |
| 4,657,138 A | | 4/1987 | Watson ....................... 206/366 |
| 4,848,587 A | | 7/1989 | Nipp .......................... 206/571 |
| 5,031,768 A | * | 7/1991 | Fischer ....................... 206/364 |
| 5,156,267 A | | 10/1992 | Yates, Jr. et al. ........... 206/364 |
| 5,411,193 A | | 5/1995 | Culp .......................... 224/252 |
| 5,566,828 A | | 10/1996 | Claes et al. ................. 206/570 |
| 5,865,314 A | | 2/1999 | Jacober ...................... 206/570 |
| 5,950,827 A | | 9/1999 | Odom et al. ................ 206/364 |
| 6,439,276 B1 | * | 8/2002 | Wood et al. ................. 141/97 |

* cited by examiner

*Primary Examiner*—David T. Fidei
(74) *Attorney, Agent, or Firm*—Fish & Richardson P.C.

(57) ABSTRACT

Cases are provided for carrying medication delivery devices such as auto-injectors, syringes or vials. The cases include a cradling structure to protect the medication delivery device from jostling and impact encountered during transport.

35 Claims, 11 Drawing Sheets

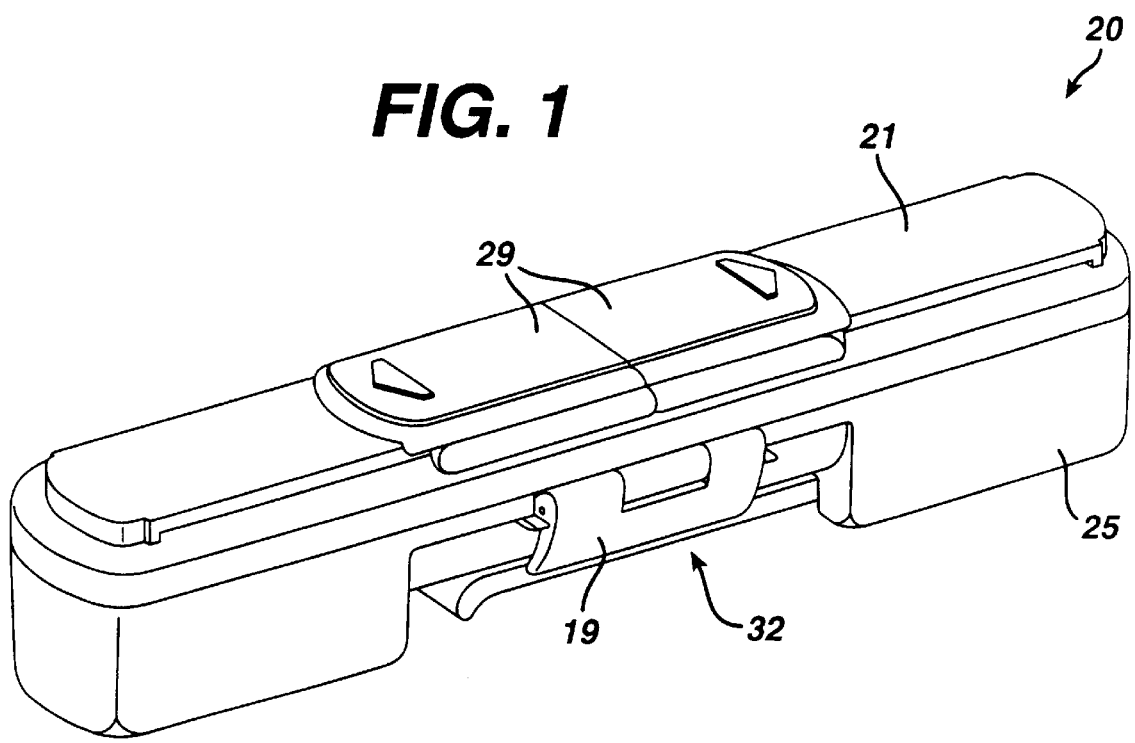

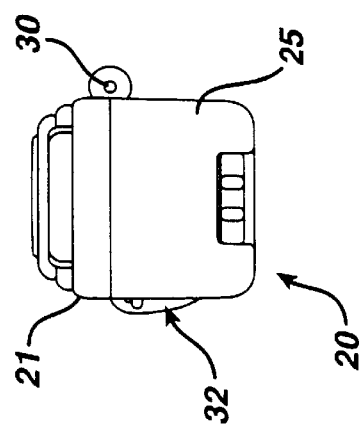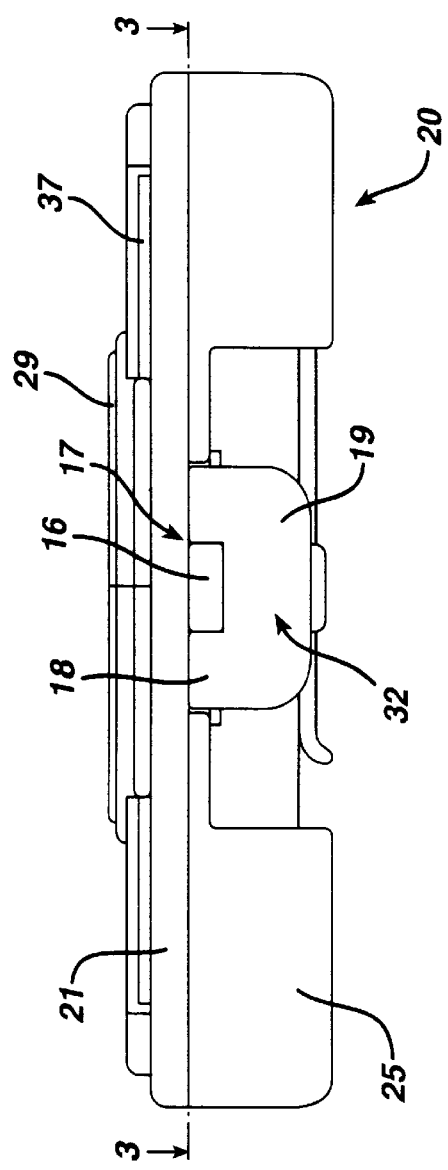

CASES FOR MEDICATION DELIVERY DEVICES

RELATED APPLICATIONS

This application claims priority from U.S. provisional application No. 60/203,880, filed May 12, 2000 and incorporated herein by reference.

TECHNICAL FIELD

This invention relates to cases for medication delivery devices, such as injection devices, e.g., auto-injectors and syringes, and vials.

BACKGROUND

Certain individuals are highly allergic to foods, including peanuts, other nuts, wheat, milk and shellfish. Others are highly allergic to the stings of insects, such as bees and wasps, to latex and/or to medications. When allergic patients are exposed to these allergens, a severe reaction may occur (anaphylaxis) which may be life-threatening if not treated immediately.

Epinephrine is generally used to treat an allergic patient at the onset of an anaphylactic reaction. Epinephrine quickly relieves bronchial swelling, constricts blood vessels, relaxes smooth muscles in the lungs, stimulates the heartbeat, and acts to reverse swelling, thus allowing the patient to function until further treatment can be obtained.

Because exposure is unpredictable, the reaction can occur quickly, and the patient may not be near medical help at the time of exposure, patients who are subject to severe anaphylactic reactions must carry epinephrine at all times. It is also necessary that the patient be able to self-administer the epinephrine while experiencing an allergic reaction. To address this need, epinephrine is generally prescribed in an auto-injector, e.g., a device commercially available under the tradename "EpiPen". The auto-injector has a spring-activated, concealed needle that, when triggered, springs forward to deliver a dose of epinephrine.

While epinephrine auto-injectors are life-saving devices when properly cared for and used, a number of safety precautions should be observed with these devices.

It is important that the auto-injector be used only for intramuscular (rather than intravenous) injection. Currently, manufacturers generally instruct that the auto-injector be used only on the patient's thigh. Injection of epinephrine into other areas can be dangerous. For example, injection into an extremity, such as a hand or foot, can shut off blood supply to that area, resulting in potential damage to the extremity. Vascular injection can also be potentially dangerous because systemic delivery of the epinephrine may cause complications in some patients due to a sharp rise in blood pressure produced by the epinephrine.

Jostling and bumping of the auto-injector while the patient is carrying the auto-injector has been known to cause accidental triggering of the spring mechanism. Accidental triggering of the auto-injector can result in injury to the patient or a caregiver or bystander. Also, accidental triggering may exhaust the epinephrine in the auto-injector, so that the epinephrine is not available when needed during an anaphylactic reaction.

The patient may suffer extreme illness and even death if the auto-injector is not in useable condition when it is needed. For example, the patient may not be able to self-inject the epinephrine if the spring-activation mechanism has been damaged by jostling or impact of the auto-injector during storage and transport by the patient.

The patient is also in danger if the medicine contained in the injector has deteriorated. Epinephrine is heat and light-sensitive, and as a result if the auto-injector is exposed to direct sunlight or extreme heat the epinephrine may oxidize, potentially rendering it ineffective. Epinephrine turns brown when oxidized, so auto-injectors are typically provided with a window to allow the patient to regularly inspect the color of the medication.

Thus, it is important that the auto-injector be stored and carried in a case that protects the auto-injector from accidental triggering, damage due to jostling or impact, and exposure to light. It is also crucial that the patient or a caregiver (potentially a small child or elderly family member) be able to remove the auto-injector from the case easily and quickly in a crisis situation.

The Epi-Pen auto-injector is generally supplied by the manufacturer in a thin plastic tube. This tube provides some protection from light, but does not cushion the auto-injector to protect it from jostling or impact. Accessory cases are available, but many of these cases are not puncture proof, may not be easily openable in a crisis situation, and/or do not adequately protect the auto-injector from jostling or impact. It may also be difficult to fit prescription or medical information into some accessory cases.

In some cases, a single dose of epinephrine may not be sufficient to treat a patient, for example if the patient is suffering from extremely severe anaphlaxis. Thus, some highly allergic patients may need to carry more than one auto-injector. Doing so can also serve as a precaution if one of the auto-injectors proves to be in an unusable condition, or is not properly administered to the patient.

SUMMARY

The present invention features cases for medical injection devices, e.g., auto-injectors, which protect the injection device from damage and protect the device and the patient from accidental triggering of the auto-injection mechanism. These cases also allow the patient or a caregiver to easily and quickly access the device in an emergency situation.

In one aspect, the invention features a case for a medication delivery device including (a) a container body defining an open chamber constructed to receive the medication delivery device; (b) a lid constructed to cover the open chamber; and (c) a cradling structure, within the chamber, constructed to hold the medication device securely in a predetermined position during transport of the case.

Some implementations may include one or more of the following features. The cradling structure includes a cradle having a curved surface. The curved surface has a curvature that substantially corresponds to the curvature of a curved portion of the medication delivery device. The cradling structure further includes a foam layer covering at least a portion of the curved surface of the cradle. The foam layer has a thickness of from about 1 to 3 mm. The foam layer is white. The cradling structure further includes a cradle guide. The cradling structure is constructed so that the medication delivery device press-fits into the cradling structure. The cradling structure is constructed so that the medication delivery device will not fall out of the cradling structure when the lid is open and the open chamber is inverted. The cradle guide is constructed to position the medication delivery device in a predetermined location within the open chamber. The case further includes a hinge joining the lid to the container body. The hinge has a sufficiently tight friction fit to allow the lid to stay open without being held open. The case further comprises a latch constructed to secure the lid in a closed position. The latch is constructed to provide a double-latching function. The latch includes a latch member, and a latch hinge joining the latch member to the lid. The latch hinge is constructed to allow the lid to stay open without being held open. The latch member includes a latch touch fastener and the container body includes a cooperating body touch fastener constructed to engage the latch touch fastener when the latch member is closed. The touch fasteners include elements of a hook and loop type fastener. The latch includes a member constructed to engage a portion of the container body in an interference fit. The medication delivery device includes an auto-injector. The container body is puncture-proof. The container body has a wall thickness of from about 1 to 4 mm. The container body includes ABS plastic. The case further includes needle ribs disposed within the chamber and constructed to receive a needle portion of the medical delivery device. The case further includes a medical history panel, and a cover constructed to conceal the medical history panel. The case further includes a belt clip mounted on the container body or lid.

In another aspect, the invention features a case for a medication delivery device including (a) a container body defining an open chamber constructed to receive the medication delivery device; (b) a lid constructed to cover the open chamber; and (c) a latch constructed to maintain the lid in a closed position and to provide a double-latching function. The latch includes (i) a latch member, the latch member including a latch touch fastener and the container body including a cooperating body touch fastener constructed to engage the latch touch fastener when the latch member is closed, (ii) a latch hinge joining the latch member to the lid, the hinge member being constructed to allow the lid to stay open without being held open, and (iii) a member constructed to engage a portion of the container body in an interference fit.

Some implementations include one or more of the following features. The touch fasteners comprise elements of a hook and loop type fastener. The case further includes a cradling structure. The cradling structure includes a cradle having a curved surface. The curved surface has a curvature that substantially corresponds to the curvature of a curved portion of the medication delivery device. The cradling structure further includes a foam layer covering at least a portion of the curved surface of the cradle. The medication delivery device includes an auto-injector.

In a further aspect, the invention features a case for a medication delivery device including (i) a container body defining an open chamber constructed to receive the medication delivery device; (ii) a lid constructed to cover the open chamber; (iii) a latch constructed to maintain the lid in a closed position and to provide a double-latching function, and (iv) a cradling structure comprising a cradle having a curved surface having a curvature that substantially corresponds to the curvature of a curved portion of the medication delivery device, and a foam layer covering at least a portion of the curved surface of the cradle. The latch includes (a) a latch member, the latch member including a latch touch fastener and the container body including a cooperating body touch fastener constructed to engage the latch touch fastener when the latch member is closed, (b) a latch hinge joining the latch member to the lid, the hinge member being constructed to allow the lid to stay open without being held open, and (c) a member constructed to engage a portion of the container body in an interference fit.

Among the advantages of the invention, the cases are very easy to open, even by individuals with compromised dexterity, e.g., an elderly person, small child, or patient suffering from an allergic reaction. When the case has been opened, the injection device will not fall out of the case, and yet is easily removed by the user. This feature reduces the risk that a user will have to pick up a dropped injection device or fumble around during a crisis.

While the case is easy to open, it also fastens securely to resist inadvertent opening, and thus prevent loss of or damage to the injection device, and to prevent accidental triggering if the device is an auto-injector.

The cases include a cushioned cradling system, which is constructed to prevent the device from falling out, as discussed above, and to prevent damage to the injection device from jostling or impact during storage and transport. In some implementations, the cushioning is white, to allow the patient to more easily determine whether the solution in the injection device has become discolored, e.g., due to oxidation.

The cases are rigid and puncture-proof, i.e., will prevent a needle from puncturing through the case to its outer surface, protecting the patient and others from puncture wounds. The cases are also lightweight and compact, allowing the case to be easily carried at all times.

In some implementations, the cases are designed to allow the patient to conveniently carry other medication, e.g., antihistamine tablets, more than one injection device, a prescription for the injection device, and important medical information.

Other features and advantages of the invention will be apparent from the description and drawings, and from the claims.

DESCRIPTION OF DRAWINGS

FIG. 1 is a perspective view of an auto-injector case according to one embodiment of the invention.

FIG. 2 is a front plan view, and FIG. 2A is a side plan view of the auto-injector case of FIG. 1.

DETAILED DESCRIPTION

Figure 1A:
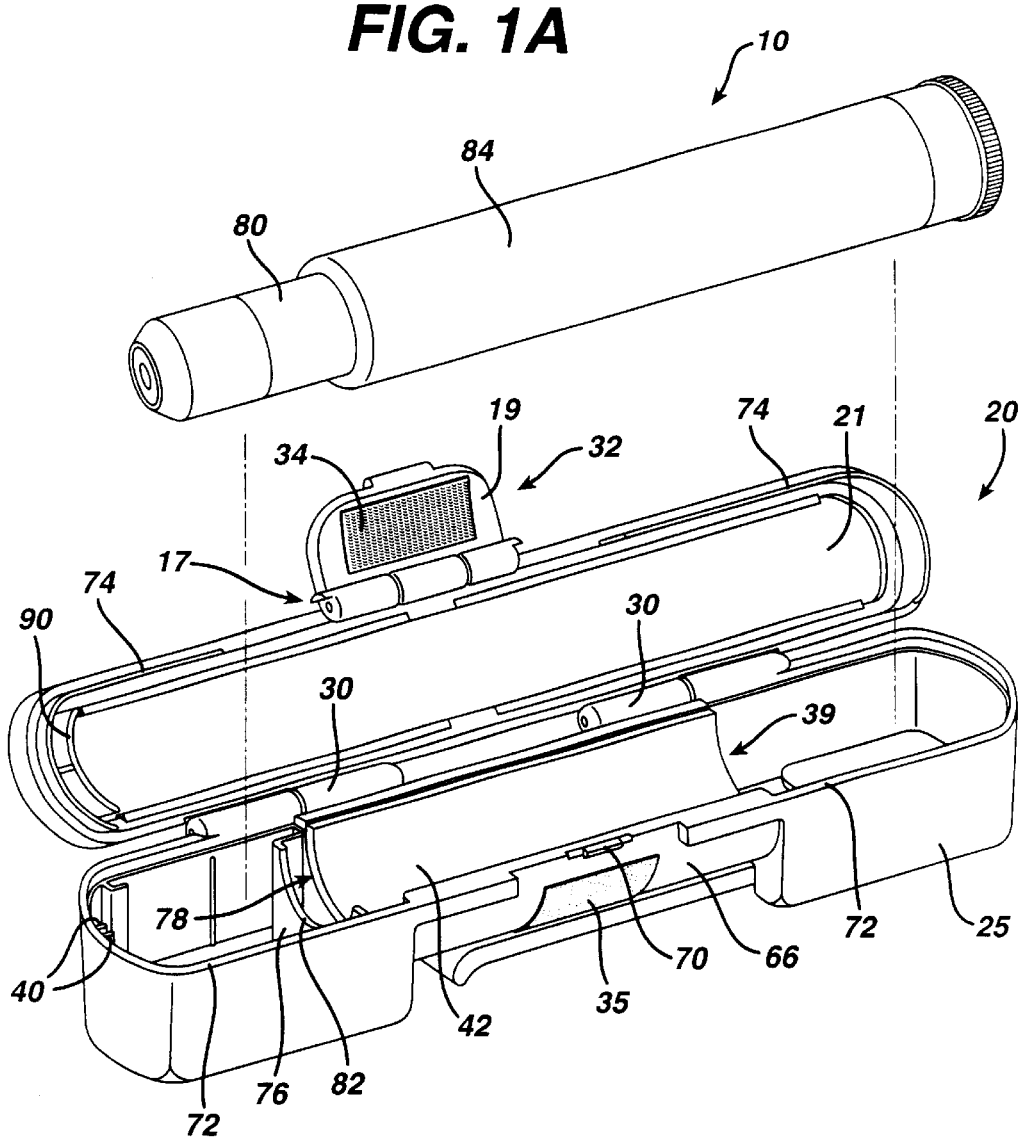
FIG. 1A is a perspective view of the auto-injector case in an open position.
Figure 1B:
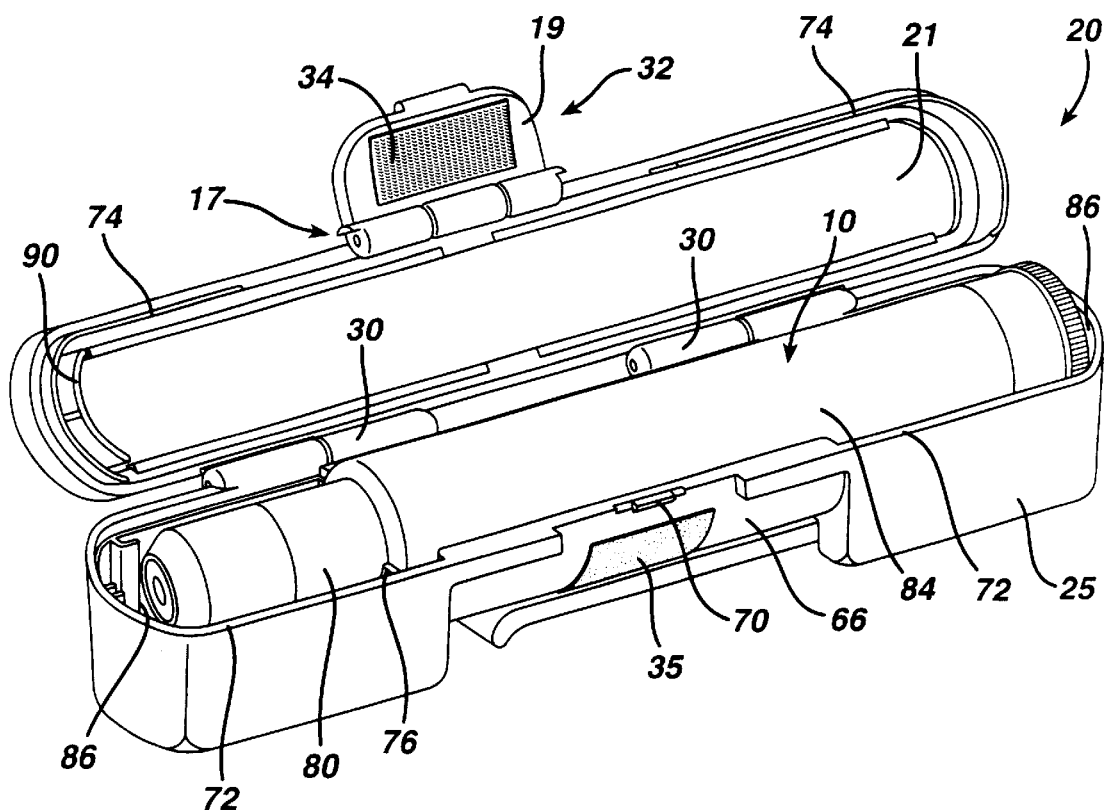
FIG. 1B is a perspective view of the open auto-injector case with an auto-injector inside.
Figure 3:
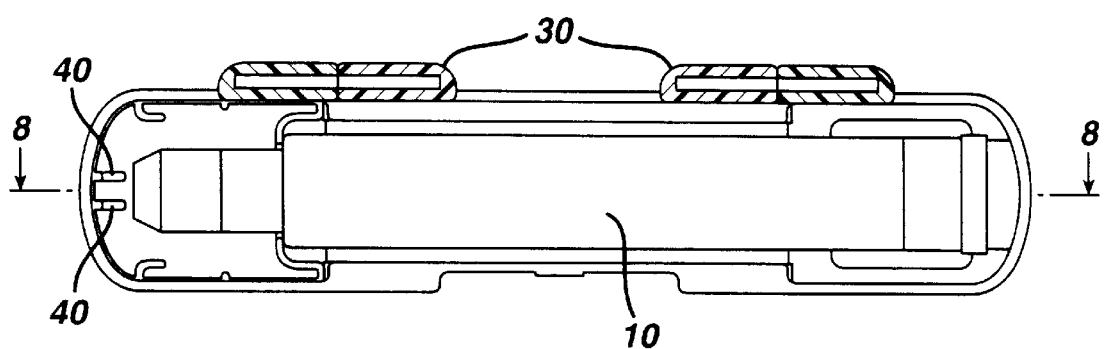
FIG. 3 is a top sectional view of the auto-injector case of FIG. 1 taken along line 3—3 in FIG. 2.

Referring to FIGS. 1–1B, an auto-injector case 20 includes a container body 25 that is constructed to receive an auto-injector 10 (FIG. 1B) in a cradling engagement, as will be discussed below. The case 20 also includes a lid 21 that securely engages the container body 25. The lid is mounted on the container using a pair of hinges 30 that are constructed to maintain the lid in a desired position after the lid has been opened by a user (i.e., to prevent the lid from self-closing if it is not held open). This feature of the hinges is generally provided by using a hinge with a tight friction fit. This feature facilitates removal of the auto-injector 10 from the case 20, and is particularly helpful for users who have a low level of dexterity.

The case 20 also includes a secure, yet easily openable, latch 32. Latch 32 provides a double latching function, securing the lid both by an interference fit with the rim of the container 25 and by engagement of a touch fastener element, as will be discussed in detail below.

The case 20 should generally be able to withstand the high impact force that may occur if the auto-injector is accidentally triggered when it is inside the case. The lid 21 and container body 25 are formed of a rigid, high-strength plastic, for example ABS, so that puncture-proofness can be provided with a relatively thin wall thickness. However, if desired, other plastics may be used, e.g., polyethylene, polypropylene, and other moldable thermoplastics. If ABS or a similar plastic is used, the wall thickness is generally from about 1 to 4 mm, more preferably about 1.0 to 2.5 mm. If other plastics are used, the wall thickness is selected to provide puncture-proofness. Puncture-proofness is further enhanced by an arcuate rib 90 that extends downwardly from the lid 21 in front of the needle end of the auto-injector 10 when the case is closed. Arcuate rib 90 is discussed further below.

Lid 21 includes a hinge portion 16, which cooperates with a corresponding hinge portion 18 on latch member 19 to provide a latch hinge 17. The latch hinge 17 is constructed to hold the latch member 19 in a fixed position when the latch member 19 is fully extended. This feature keeps the latch member 19 from flopping down when the user is trying to open the lid, further enhancing the ease with which the lid can be opened. When the latch member 19 is in its fixed position it also serves as a handle which can be used to lift the lid 21.

Figure 6:
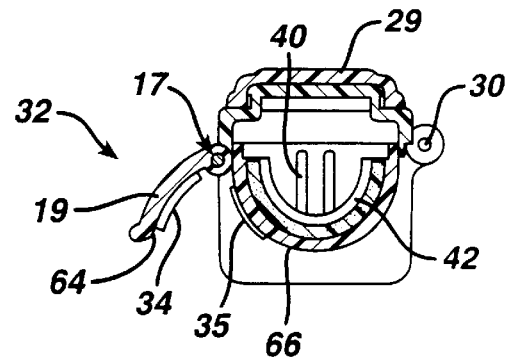
FIG. 6 is a sectional view of the auto-injector case of FIG. 1 taken along line 6—6 in FIG. 4, showing the latch in an open position.

Referring to FIG. 6, latch member 19 includes a touch fastener strip 34 on its inner surface 64. Touch fastener strip 34 is positioned for engagement with a cooperating touch fastener strip 35 on the outer surface 66 of container body 25. Touch fastener strips 34 and 35 may be, for example, male and female portions of a hook-and-loop fastener, for example fasteners commercially available under the tradename VELCRO. The engagement of the touch fastener holds the latch member securely in place against the outer surface of the container body 25, while allowing the latch member to be easily disengaged by a user.

As shown in FIG. 1A, hinge portion 16 includes a groove 68 that is constructed to engage ridge 70 on rim 72 of the container body 25 in an interference fit to further secure the lid in a closed position. This provides a back-up latching mechanism, in the event that the touch fastener strips 34, 35 do not engage when the user closes the lid, or in the unlikely event that the touch fastener becomes accidentally disengaged. The engagement of ridge 70 in groove 68 is secure against accidental disengagement, but easily snaps open in response to a user applying upward pressure to the latch member 19. This snap fit is further enhanced by an interference engagement between rim 74 of lid 21 and rim 72 of the container body 25.

As noted above, the container body 25 includes a cradling structure that prevents jostling and bumping of the auto-injector when it is carried by the patient. Referring to FIGS. 1A and 6, the inner surface of container body 25 includes a cradle 39 that has a curved surface with a curvature that conforms to the curvature of the auto-injector. For an Epi-Pen auto-injector, a suitable radius of curvature R is about 8 to 10 mm, e.g., about 9 mm.

A foam pad 42 is mounted on the curved surface of the cradle 39, to provide a snug, resilient engagement between the auto-injector and the cradle 39. Preferably, the foam pad 42 and cradle 39 are dimensioned so that the auto-injector press-fits into the cradle in response to gentle pressure by the user, or in response to the pressure that is applied to the auto-injector when the lid is closed, if the user has not already pressed the auto-injector into the cradle.

The foam pad 42 cushions the auto-injector against impact, further reducing the likelihood of accidental triggering. By resiliently engaging the auto-injector, the foam pad 42 also prevents the auto-injector from falling out of the container when the lid is opened. Preferably, the auto-injector fits sufficiently snugly into the cradle 39 so that the open case 20 (FIG. 1B) can be completely inverted without the auto-injector falling out. By reducing the likelihood that the auto-injector will be dropped when the case is open, this feature also reduces the danger that precious treatment time will be wasted while the patient or a caregiver struggles to find a dropped auto-injector. Similarly, this feature reduces the likelihood of accidental triggering, which may occur if an auto-injector is dropped.

Suitable foams include closed cell, low to medium density foams. Suitable foams have sufficient compressibility to provide the cushioning and resilient engagement features discussed above. Suitable foams include polyethylene foams. Preferably the foam does not contain any latex, to avoid allergic reactions. The radius of curvature of the cradle can be adjusted based on the density of the foam to provide a desired degree of resilient engagement (generally, lower density foams will require a smaller radius cradle).

The foam pad is sufficiently thick to provide cushioning and resilient engagement, but sufficiently thin so that the auto-injector can be readily removed from the cradle by the patient or a caregiver. Preferably, the foam pad is from about 1 to 3 mm thick when uncompressed, more preferably about 1.25 to 1.75 mm thick.

Preferably, the foam pad is white, so that the patient or caregiver can easily observe whether the liquid in the auto-injector is clear, as it should be for an epinephrine injector, or whether the liquid is colored, indicating oxidation and/or deterioration.

In some applications, it may be useful to provide additional foam padding on the inside surface of lid 21. If such padding is used, it should be dimensioned and positioned so that the lid will close properly.

Figure 4:
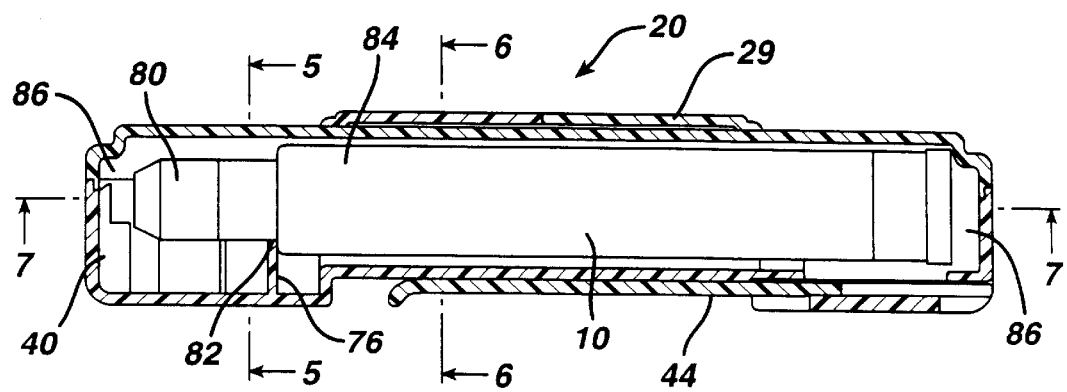
FIG. 4 is a sectional view of the auto-injector case of FIG. 1 taken along line 4—4 in FIG. 3.
Figure 5:
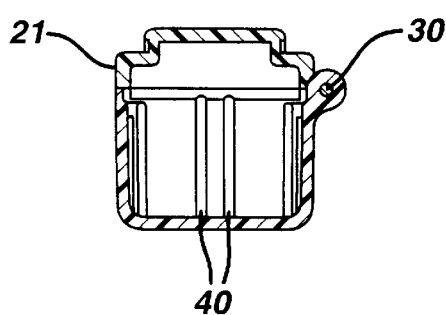
FIG. 5 is a sectional view of the auto-injector case of FIG. 1 taken along line 5—5 in FIG. 4.

Referring to FIGS. 1A, 1B and 4, the container body 25 also includes a cradle guide 76 that extends generally perpendicular to the longitudinal axis of the auto-injector 10 when the auto-injector is in place (FIG. 1B). Cradle guide 76 includes a curved opening 78 through which the smaller diameter, forward portion 80 of the auto-injector can extend. Curved edge 82 of cradle guide 76 acts as a stop, properly positioning the larger diameter portion 84 of the auto-injector in the cradle 39 for easy removal of the auto-injector. The cradle guide positions the auto-injector so that there is a gap 86 on each end of the auto-injector (FIG. 1B), allowing a user to easily slip a fingertip into the gap to lever the end of the auto-injector out of the cradle 39.

Figure 7:
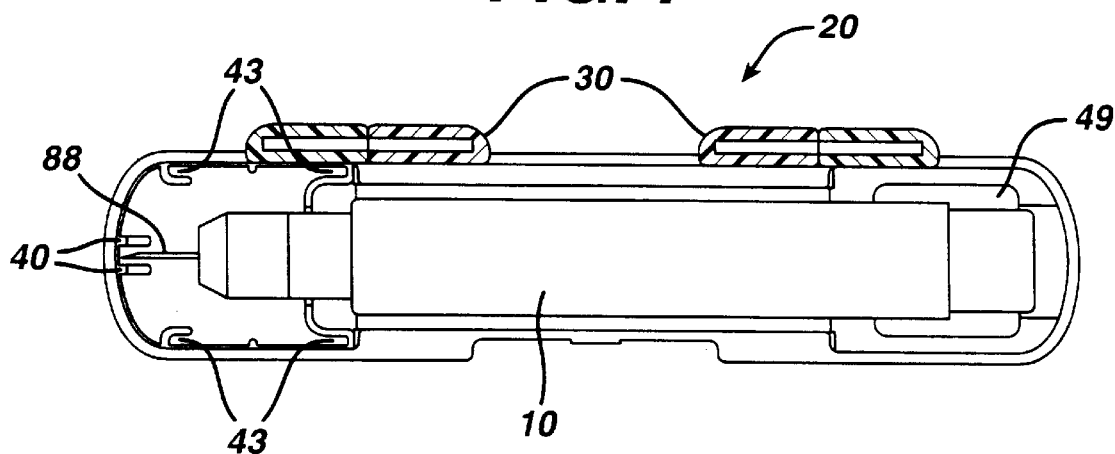
FIG. 7 is a sectional view of the auto-injector case of FIG. 1 taken along line 7—7 in FIG. 4, with a used injector pin in the case.
Figure 8:
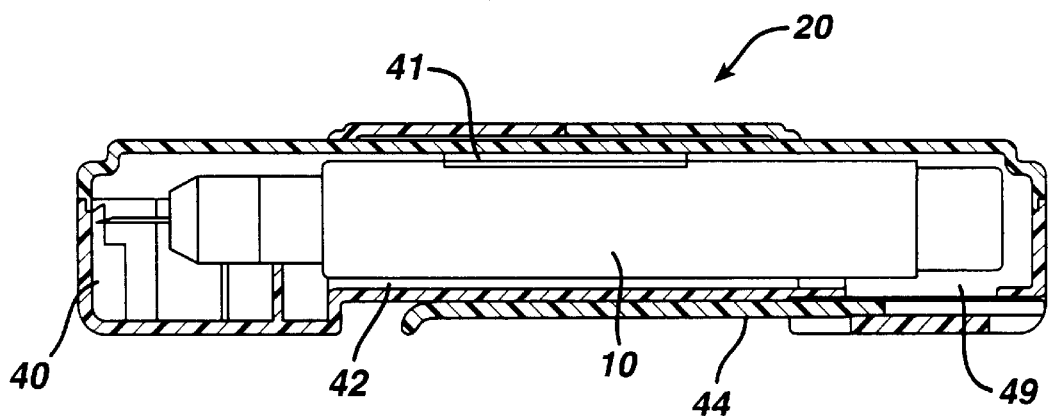
FIG. 8 is a sectional view of the auto-injector case of FIG. 1 taken along line 8—8 in FIG. 3, with a used injector pin in the case.

After the auto-injector has been triggered, whether intentionally or unintentionally, the needle is exposed and remains exposed, thus creating a danger of puncture wounds. If the auto-injector has been triggered intentionally, it is necessary for the patient to bring the auto-injector to the treating physician so that the physician will know how much epinephrine has been taken. As shown in FIGS. 7 and 8, the container body includes needle ribs 40, which enclose the needle 88 during transport, providing a safe, puncture-proof way to carry the used auto-injector to the hospital or treating physician. The needle ribs 40 also reduce the risk of accidentally stabbing a finger when the used auto-injector is removed from the case, by preventing the user from grasping the needle by the tip during removal. Needle ribs 40 are preferably substantially flat plastic members, integrally molded with the container body 25 of the same puncture-proof material. Preferably the ribs are from about 1.0 to 2.5 mm thick.

The lid 21 includes an arcuate rib 90, extending downwardly from the inner surface of the lid, which is positioned in front of the needle end of the auto-injector when the lid is closed. Arcuate rib 90 enhances the puncture-proofness of the case 20, because in the event of accidental triggering of the auto-injector the arcuate rib 90 will either push the needle 88 down between the ribs, or force it partially back into the auto-injector, depending upon the angle at which the needle is discharged. The arcuate rib 90 is positioned so that it will not force the needle fully back into the auto-injector, so that it will be possible for the user to observe that accidental triggering has occurred. If the arcuate rib is formed of ABS or a plastic with similar mechanical properties, the arcuate rib is preferably about 1 to 3 mm thick, e.g., about 2 mm. The arcuate rib is mounted on a support that is positioned directly in front of the needle of the auto-injector, to further enhance puncture-proofness. The support preferably has a thickness of from about 1 to 3 mm.

In some cases, a patient may have an allergic reaction that is not severe enough to warrant injection, and yet requires treatment, e.g., with an antihistamine such as BENADRYL antihistamine. To allow the patient to keep all of his or her emergency allergy medication together in one place, the container body 25 also includes medication slots 43 for holding two push-through packets containing antihistamine tablets.

Some emergency medical personnel are reluctant to administer an epinephrine injection without a prescription. To avoid this problem, the container body 25 is preferably sized to permit the patient to carry a folded prescription in prescription storage location 49.

Figure 9:
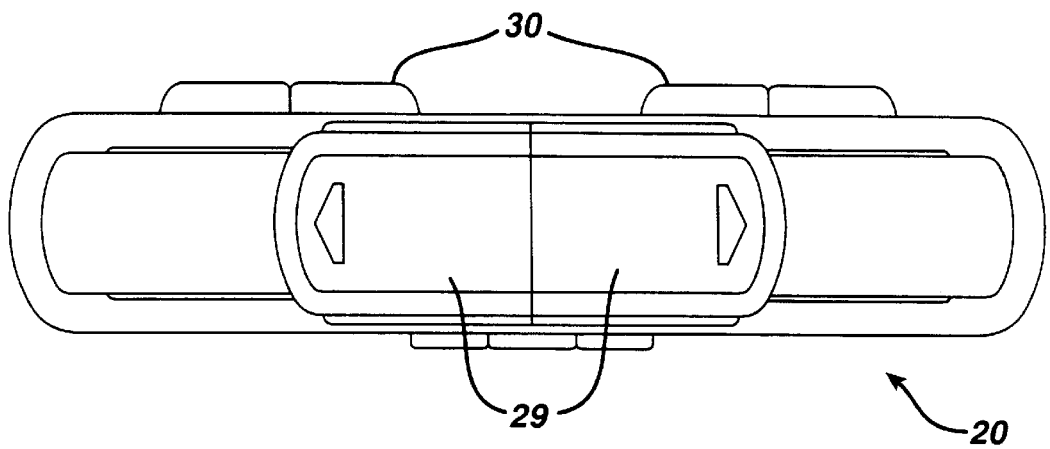
FIG. 9 is a top plan view of the auto-injector case of FIG. 1 with the sliders closed.
Figure 10:
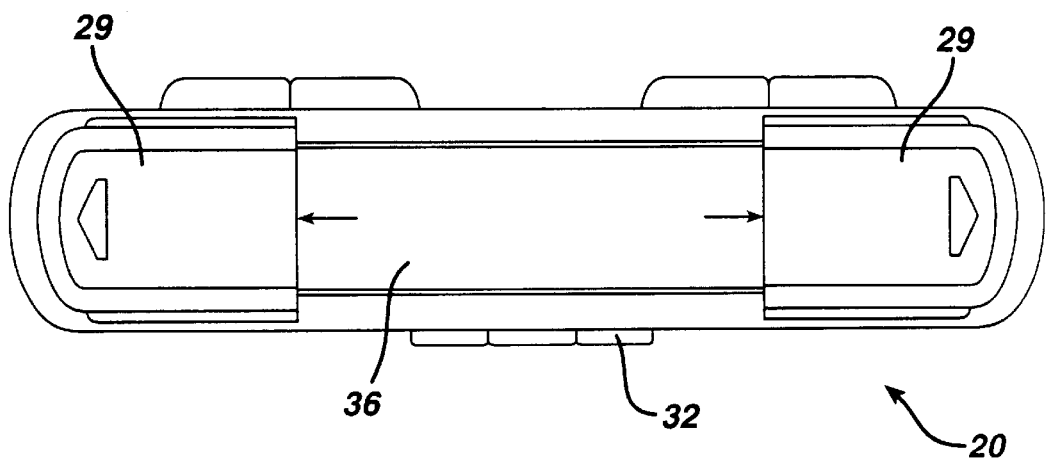
FIG. 10 is a top plan view of the auto-injector case of FIG. 1 with the sliders open.

To allow the patient to provide medical history information to a caregiver in an emergency, while keeping the information private at other times, the case 20 includes sliders 29 which are movably mounted on lid 21 to slide along tracks 37 (FIGS. 9 and 10). In the open position, shown in FIG. 10, the sliders 29 reveal a medical history panel 36. When the sliders are in the closed position, shown in FIG. 9, the information on the medical history panel 36 remains private.

Figure 13:
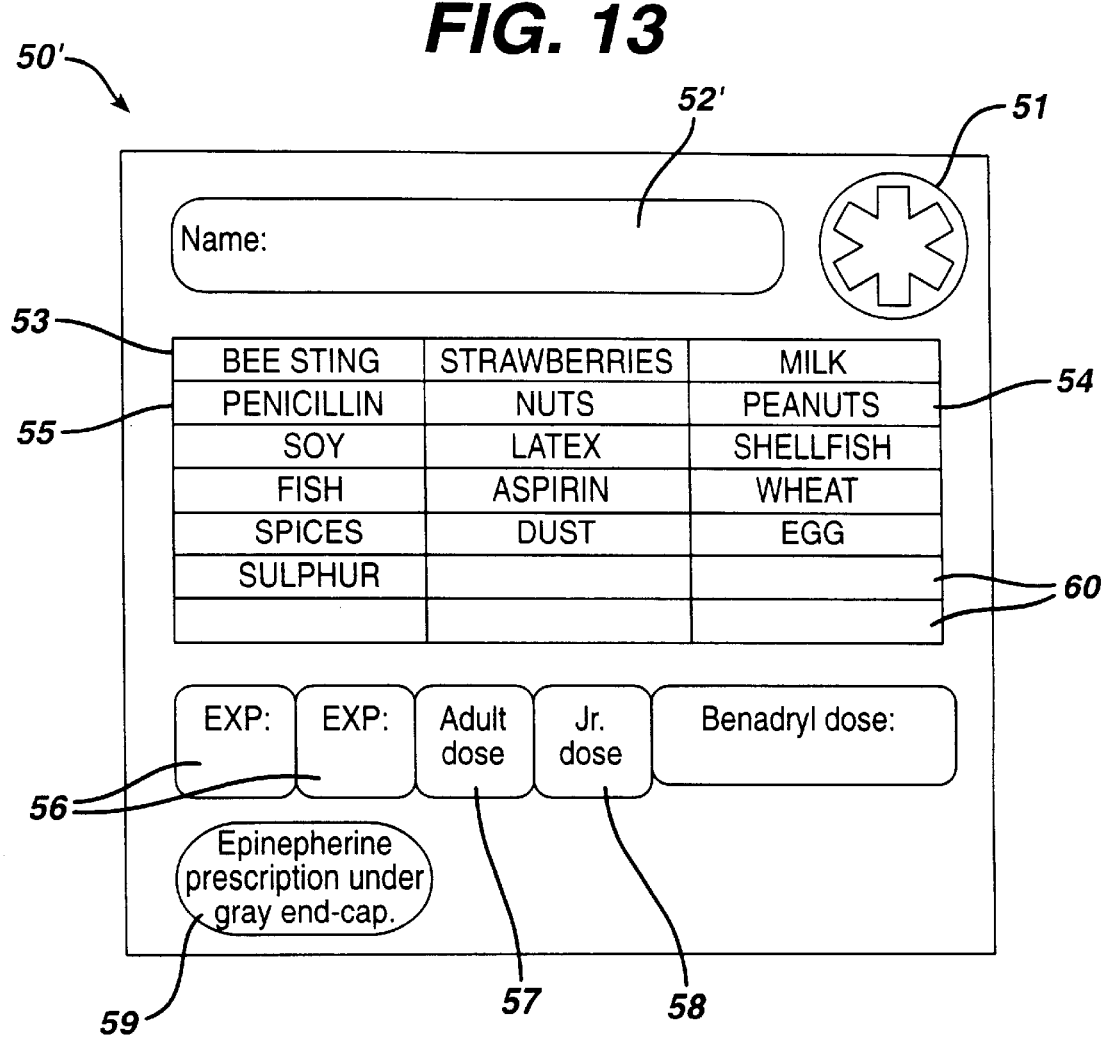
FIGS. 13 and 13A are examples of labels containing a patient's medical information.
Figure 13A:
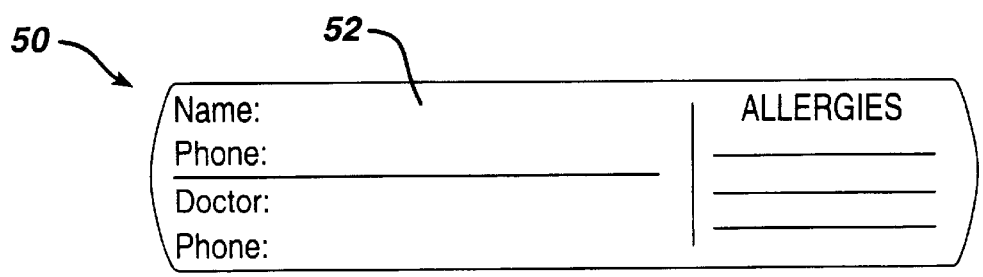

A label 50, e.g., as shown in FIG. 13A, can be mounted on the medical history panel, giving the patient's medical and emergency information 52, e.g., name, phone number, allergies, and doctor's name and phone number.

A more detailed label 50' that may be used is shown in FIG. 13. This label includes medical information symbols 51, a name plate 52', areas that can be checked off or circled to indicate foods or materials to which the patient is allergic, e.g., bee sting (53), peanuts (54) or penicillin (55), and blank areas 60 to allow the patient to fill in other foods/materials that are not listed. Label 50' also includes a box 56 to indicate the expiration date of the auto-injector, identifies the auto-injector as an adult dosage (57) or junior dosage (58), and notifies a caregiver that a prescription is located in the case (59).

Labels 50, 50' are preferably moisture resistant, and users are instructed to use an indelible marker to fill in the information.

The case 20 may include various accessories to enable a patient to have it handy at all times.

For example, a magnet (not shown) can be provided, e.g., on the bottom outer surface of the container body, to allow the case 20 to be removably mounted on a refrigerator, filing cabinet or other convenient metal area.

Figure 11:
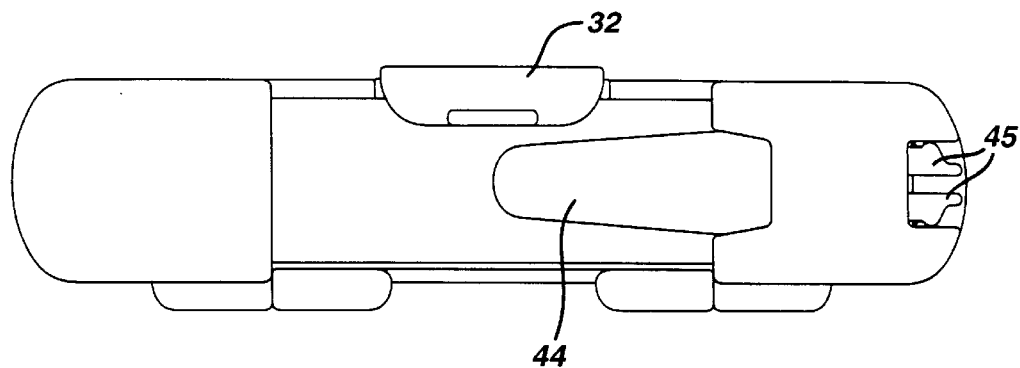
FIG. 11 is a bottom plan view of the auto-injector case of FIG. 1 with a belt clip in place.
Figure 12:
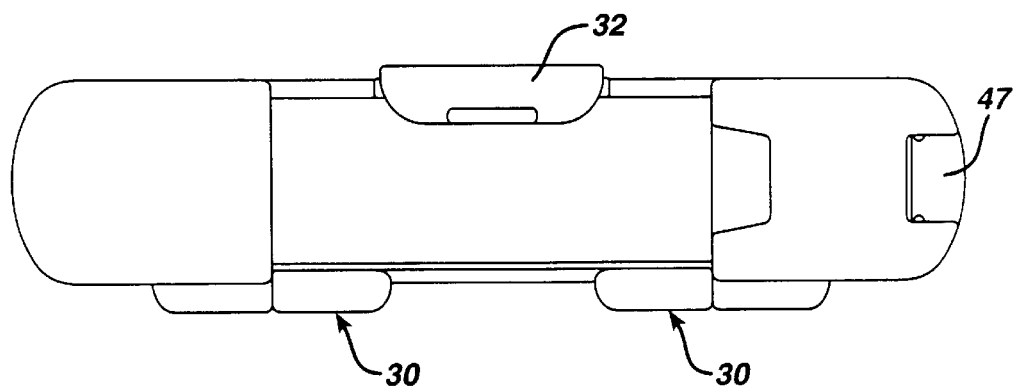
FIG. 12 is a bottom plan view of the auto-injector case of FIG. 1 with the belt clip omitted.

Also, as shown in FIGS. 4, 8 and 11, the case 20 may include a removable belt clip 44. Belt clip 44 may be of any suitable material, e.g., plastic or metal, and is removably inserted into belt clip hole 46 by compressing the belt clip prongs 45 (FIG. 11). Belt clip hole 46 is covered with a cap 47 (FIG. 12) when the belt clip is not in use.

The case 20 may also be provided with a self-adhering strap (not shown), e.g., of a touch fastener material such as VELCRO fastener material. The self-adhering strap can be threaded through the belt clip hole 46 and attached to itself to form a loop. A hook, e.g., a snap-hook, can be attached to the loop to allow case 20 to be hung from a knapsack, wall hook or other location. The self-adhering strap can also be looped through the belt clip holes of two cases, to hold the cases together, e.g., for patients who carry a second auto-injector as a back-up or for caregivers who are responsible for the storage of injectors for more than one user.

Other embodiments are within the scope of the following claims.

For example, while the discussion above has focused on cases for epinephrine auto-injectors, the cases described above are suitable for use with auto-injectors containing other types of medication, e.g., antidotes for chemical poisoning such as are used in military applications. Also, while the cases described above are particularly suitable for use with auto-injectors, they may also be used with other types of medication delivery devices, for example, syringes containing medications such as insulin or morphine, and fragile medication-containing vials. If the case is used with a medication that must be kept cold, e.g., insulin, space can be provided in the case for a tiny cold pack Moreover, while the latch in the implementation described above is secured using a touch fastener, any desired type of fastener may be used, as long as the fastener is relatively secure and can be easily disengaged by a user. Other suitable fasteners include snaps, magnets and pressure sensitive adhesives.

Additionally, the sliders discussed above may be replaced by a flap or other structure that allows the patient information to be concealed, or may be omitted and the patient information provided inside the case.

Figure 14:
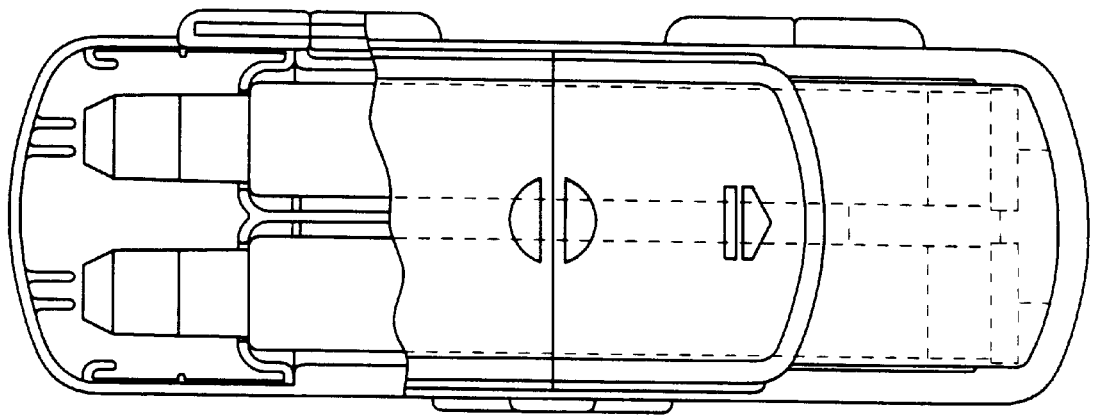
FIG. 14 is a top view with the lid partially broken away.
Figure 15:
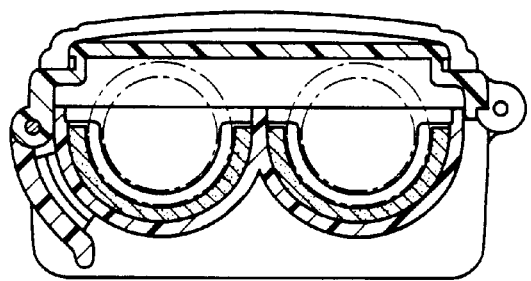
FIG. 15 is a cross-sectional view of an auto-injector case for carrying two auto-injectors.

While the case described above is sized to hold a single auto-injector, in other implementations the case is sized to hold two auto-injectors side by side. In these implementations, the case includes two cradles and two sets of needle ribs, e.g., as shown in FIGS. 14 and 15.

What is claimed is:

1. A case for a medication delivery device comprising:
    a container body defining an open chamber constructed to receive the medication delivery device;
    a lid constructed to cover the open chamber; and
    a molded plastic cradling structure, within the chamber, constructed to hold the medication device securely in a predetermined position during transport of the case, the cradling structure including a curved surface and a foam layer covering at least a portion of the curved surface of the cradling structure.

2. The case of claim 1 wherein the curved surface has a curvature that substantially corresponds to the curvature of a curved portion of the medication delivery device.

3. The case of claim 1 wherein the foam layer has a thickness of from about 1 to 3 mm.

4. The case of claim 1 wherein the foam layer is white.

5. The case of claim 1 wherein the cradling structure further comprises a cradle guide.

6. The case of claim 1 wherein the cradling structure is constructed so that the medication delivery device press-fits into the cradling structure.

7. The case of claim 1 wherein the cradling structure is constructed so that the medication delivery device will not fall out of the cradling structure when the lid is open and the open chamber is inverted.

8. The case of claim 5 wherein the cradle guide is constructed to position the medication delivery device in a predetermined location within the open chamber.

9. The case of claim 1 further comprising a hinge joining the lid to the container body.

10. The case of claim 9 wherein the hinge has a sufficiently tight friction fit to allow the lid to stay open without being held open.

11. The case of claim 1 further comprising a latch constructed to secure the lid in a closed position.

12. The case of claim 11 wherein the latch is constructed to provide a double-latching function.

13. The case of claim 11 wherein the latch includes a latch member, and a latch hinge joining the latch member to the lid.

14. The case of claim 13 wherein the latch hinge is constructed to allow the lid to stay open without being held open.

15. The case of claim 13 wherein the latch member includes a latch touch fastener and the container body includes a cooperating body touch fastener constructed to engage the latch touch fastener when the latch member is closed.

16. The case of claim 15 wherein the touch fasteners comprise elements of a hook and loop type fastener.

17. The case of claim 11 wherein the latch includes a member constructed to engage a portion of the container body in an interference fit.

18. The case of claim 1 wherein the medication delivery device comprises an auto-injector.

19. The case of claim 1 wherein the container body is puncture-proof.

20. The case of claim 1 wherein the container body has a wall thickness of from about 1 to 4 mm.

21. The case of claim 1 wherein the container body comprises ABS plastic.

22. The case of claim 1 further comprising needle ribs disposed within the chamber and constructed to receive a needle portion of the medical delivery device.

23. The case of claim 1 further comprising a medical history panel, and a cover constructed to conceal the medical history panel.

24. The case of claim 1 further comprising a belt clip mounted on the container body or lid.

25. A case for a medication delivery device comprising:
    a container body defining an open chamber constructed to receive the medication delivery device;
    a lid constructed to cover the open chamber; and
    a latch constructed to maintain the lid in a closed position and to provide a double-latching function, the latch comprising
        (a) a latch member, the latch member including a latch touch fastener and the container body including a cooperating body touch fastener constructed to engage the latch touch fastener when the latch member is closed,
        (b) a latch hinge joining the latch member to the lid, the hinge member being constructed to allow the lid to stay open without being held open, and
        (c) a member constructed to engage a portion of the container body in an interference fit.

26. The case of claim 25 wherein the touch fasteners comprise elements of a hook and loop type fastener.

27. The case of claim 25 further including a cradling structure.

28. The case of claim 27 wherein the cradling structure comprises a cradle having a curved surface.

29. The case of claim 28 wherein the curved surface has a curvature that substantially corresponds to the curvature of a curved portion of the medication delivery device.

30. The case of claim 28 wherein the cradling structure further comprises a foam layer covering at least a portion of the curved surface of the cradle.

31. The case of claim 25 wherein the medication delivery device comprises an auto-injector.

32. A case for a medication delivery device comprising:
    (i) a container body defining an open chamber constructed to receive the medication delivery device;
    (ii) a lid constructed to cover the open chamber;
    (iii) a latch constructed to maintain the lid in a closed position and to provide a double-latching function, the latch comprising
        (a) a latch member, the latch member including a latch touch fastener and the container body including a cooperating body touch fastener constructed to engage the latch touch fastener when the latch member is closed,
        (b) a latch hinge joining the latch member to the lid, the hinge member being constructed to allow the lid to stay open without being held open, and
        (c) a member constructed to engage a portion of the container body in an interference fit; and
    (iv) a cradling structure comprising a cradle having a curved surface having a curvature that substantially corresponds to the curvature of a curved portion of the medication delivery device, and a foam layer covering at least a portion of the curved surface of the cradle.

33. The case of claim 32 wherein the medication delivery device comprises an auto-injector.

34. A case for a medication delivery device including an auto-injector, the case comprising:

a container body defining an open chamber constructed to receive the medication delivery device;

a lid constructed to cover the open chamber;

a cradling structure, within the chamber, constructed to hold the medication device securely in a predetermined position during transport of the case, the cradling structure including curved surface and a foam layer covering at least a portion of the curved surface of the cradling structure; and a cradle guide that extends generally perpendicular to the longitudinal axis of the auto-injector when the auto-injector is in place in the chamber, the cradle guide including a curved opening through which a forward portion of the auto-injector can extend and a curved edge configured to act as a stop, properly positioning the auto-injector in the cradle structure for easy removal of the auto-injector from the case by providing a gap on each end of the auto-injector, thereby allowing a user to easily slip a fingertip into the gap to lever the end of the auto-injector out of the cradle structure.

35. A case for a medication delivery device comprising an auto-injector, the case comprising:

a puncture-proof container body defining an open chamber constructed to receive the medication delivery device;

a lid constructed to cover the open chamber; and a molded plastic cradling structure, within the chamber, constructed so that the medication delivery device press-fits into the cradling structure to hold the medication device securely in a predetermined position during transport of the case, the cradling structure including a curved surface and a foam layer covering at least a portion of the curved surface of the cradling structure.

\* \* \* \* \*